United States Patent
Ginat Eliash et al.

(10) Patent No.: US 12,432,236 B2
(45) Date of Patent: Sep. 30, 2025

(54) DETECTING COMPROMISED MEDICAL DEVICES

(71) Applicant: Cynerio Israel Ltd., Ramat Gan (IL)

(72) Inventors: Reut Ginat Eliash, Givatayim (IL); Roey Vilnai, Boston, MA (US); Daniel Brodie, Modiln (IL); Leon Lerman, New York, NY (US)

(73) Assignee: Cynerio Israel Ltd., Ramat Gan (IL)

( * ) Notice: Subject to any disclaimer, the term of this patent is extended or adjusted under 35 U.S.C. 154(b) by 349 days.

(21) Appl. No.: 18/135,794

(22) Filed: Apr. 18, 2023

(65) Prior Publication Data
US 2024/0356940 A1    Oct. 24, 2024

(51) Int. Cl.
*H04L 9/40* (2022.01)
*G16H 40/40* (2018.01)

(52) U.S. Cl.
CPC ......... *H04L 63/1425* (2013.01); *G16H 40/40* (2018.01); *H04L 63/0428* (2013.01); *H04L 63/1416* (2013.01); *H04L 63/1433* (2013.01)

(58) Field of Classification Search
CPC ............. H04L 63/1425; H04L 63/0428; H04L 63/1416; H04L 63/1433; G16H 40/40
See application file for complete search history.

(56) References Cited

U.S. PATENT DOCUMENTS

| | | | |
|---|---|---|---|
| 10,938,783 B2 * | 3/2021 | Thompson | H04L 63/0263 |
| 2012/0083298 A1 * | 4/2012 | Park | H04W 12/04 455/500 |
| 2019/0238575 A1 * | 8/2019 | Hodgman | H04L 63/1433 |
| 2019/0394645 A1 * | 12/2019 | Knaappila | H04W 12/06 |
| 2021/0385253 A1 * | 12/2021 | Shivamoggi | H04L 63/1408 |
| 2022/0337488 A1 * | 10/2022 | Najman | G06N 5/04 |

* cited by examiner

*Primary Examiner* — Chau Le

(57) ABSTRACT

There is provided a computer implemented method of detecting a malicious connection of a medical device, comprising: monitoring packets of network traffic generated by a plurality of medical devices connected to a network by a plurality of connections, for a connection of a medical device: selecting a device cluster from a plurality of device clusters according to attributes of the medical device and/or network activity of internal and/or external connection of the medical device, extracting a plurality of categorical features, computing a distance from the plurality of categorical features to a nearest connection cluster of a plurality of connection clusters of sample connections of sample medical devices of the selected device cluster, and identifying the connection as malicious when the distance is above a threshold.

19 Claims, 6 Drawing Sheets

DETECTING COMPROMISED MEDICAL DEVICES

BACKGROUND

The present invention, in some embodiments thereof, relates to cybersecurity and, more specifically, but not exclusively, to systems and methods for detecting compromised medical devices.

Computers connected to a network may become infected by malware. Such malware infected computers may experience abnormal operations, and/or may infect other network connected devices. Approaches for quickly identifying compromised network connected devices reduce likelihood of infection by other network connected devices and/or may reduce damage incurred due to the infected network connected device.

SUMMARY

According to a first aspect, a computer implemented method of detecting a malicious connection of a medical device, comprises: monitoring packets of network traffic generated by a plurality of medical devices connected to a network by a plurality of connections, for a connection of a medical device: selecting a device cluster from a plurality of device clusters according to attributes of the medical device and/or network activity of internal and/or external connection of the medical device, extracting a plurality of categorical features, computing a distance from the plurality of categorical features to a nearest connection cluster of a plurality of connection clusters of sample connections of sample medical devices of the selected device cluster, and identifying the connection as malicious when the distance is above a threshold.

According to a second aspect, system for detecting a malicious connection of a medical device, comprises: at least one processor executing a code for: monitoring packets of network traffic generated by a plurality of medical devices connected to a network by a plurality of connections, for a connection of a medical device: selecting a device cluster from a plurality of device clusters according to attributes of the medical device and/or network activity of internal and/or external connection of the medical device, extracting a plurality of categorical features, computing a distance from the plurality of categorical features to a nearest connection cluster of a plurality of connection clusters of sample connections of sample medical devices of the selected device cluster, and identifying the connection as malicious when the distance is above a threshold.

According to a third aspect, a non-transitory medium storing program instructions for detecting a malicious connection of a medical device, which when executed by at least one processor, cause the at least one processor to: monitor packets of network traffic generated by a plurality of medical devices connected to a network by a plurality of connections, for a connection of a medical device: select a device cluster from a plurality of device clusters according to attributes of the medical device and/or network activity of internal and/or external connection of the medical device, extract a plurality of categorical features, compute a distance from the plurality of categorical features to a nearest connection cluster of a plurality of connection clusters of sample connections of sample medical devices of the selected device cluster, and identify the connection as malicious when the distance is above a threshold.

In a further implementation form of the first, second, and third aspects, further comprising, determining whether protected health information (PHI) is sent and/or received over the connection of the medical device, and prioritizing the connection of the medical device over other connections over which PHI is not sent and/or received.

In a further implementation form of the first, second, and third aspects, further comprising in response to identifying the connection as malicious, generating instructions for isolating the medical device from other devices on the network.

In a further implementation form of the first, second, and third aspects, further comprising: computing the plurality of device clusters by clustering a plurality of sample medical devices according to attributes of each sample medical device, and/or network activity of internal and/or external connections of each sample medical device, for each respective device cluster, computing the plurality of connection clusters by clustering categorical features extracted for each sample connection of each sample device of the respective device cluster.

In a further implementation form of the first, second, and third aspects, the medical device are selected from a group including: type of the medical device, model of the medical device, manufacturer of the medical device, and operating system running on the medical device.

In a further implementation form of the first, second, and third aspects, the sample medical devices and the plurality of sample connections are benign and exclude malicious connections and compromised medical devices.

In a further implementation form of the first, second, and third aspects, the sample medical devices are at least one of: from different healthcare organization, and from different environments.

In a further implementation form of the first, second, and third aspects, further comprising computing the threshold by: monitoring packets of network traffic generated by a plurality of benign medical devices connected to the network by a plurality of benign connections not infected by malware, computing a plurality of benign distances for the plurality of benign connections, each benign distance computed by the selecting the device, the extracting, and the computing the distance, accessing synthetic data of packets of network traffic that mimics output of malicious medical devices infected by malware to a plurality of malicious connections, computing a plurality of malicious distances for the plurality of malicious connections, each malicious distance computed by the selecting the device, the extracting, and the computing the distance, and setting the threshold for statistically separating between a distribution of the plurality of benign distances and the plurality of malicious distances.

In a further implementation form of the first, second, and third aspects, setting the threshold comprises computing a similarity score indicating similarity between each of the plurality of malicious distances and the plurality of benign distances, identifying a certain malicious distance having a maximum similarity with a certain benign distance, and setting the threshold as the certain malicious distance.

In a further implementation form of the first, second, and third aspects, the plurality of features are extracted without accessing payload of the packets of the network traffic generated by the plurality of medical devices.

In a further implementation form of the first, second, and third aspects, the monitoring is performed on a centralized node through which the network traffic generated by the plurality of medical devices flows.

In a further implementation form of the first, second, and third aspects, the plurality of categorical features include network features extracted as metadata from the packets.

In a further implementation form of the first, second, and third aspects, the plurality of categorical features include enrichment features extracted from external data sources correlated with the packets.

In a further implementation form of the first, second, and third aspects, the plurality of categorical features include expert features calculated based on expert data.

In a further implementation form of the first, second, and third aspects, the plurality of medical devices are selected from a group including: imaging devices, ventilators, blood gas analyzers, ECG monitors.

In a further implementation form of the first, second, and third aspects, further comprising: creating a reduced set of features by selecting dominant features and excluding non-dominant features from the plurality of categorical features, wherein a dominant feature appears in at least as many connections as a number of unique labels in the feature to a power of negative one, wherein the distance is computed using the reduced set of features.

In a further implementation form of the first, second, and third aspects, further comprising setting values of the plurality of categorical features that are missing and/or are non-dominant to a unique value that is randomly generated.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DETAILED DESCRIPTION

Figure 1:
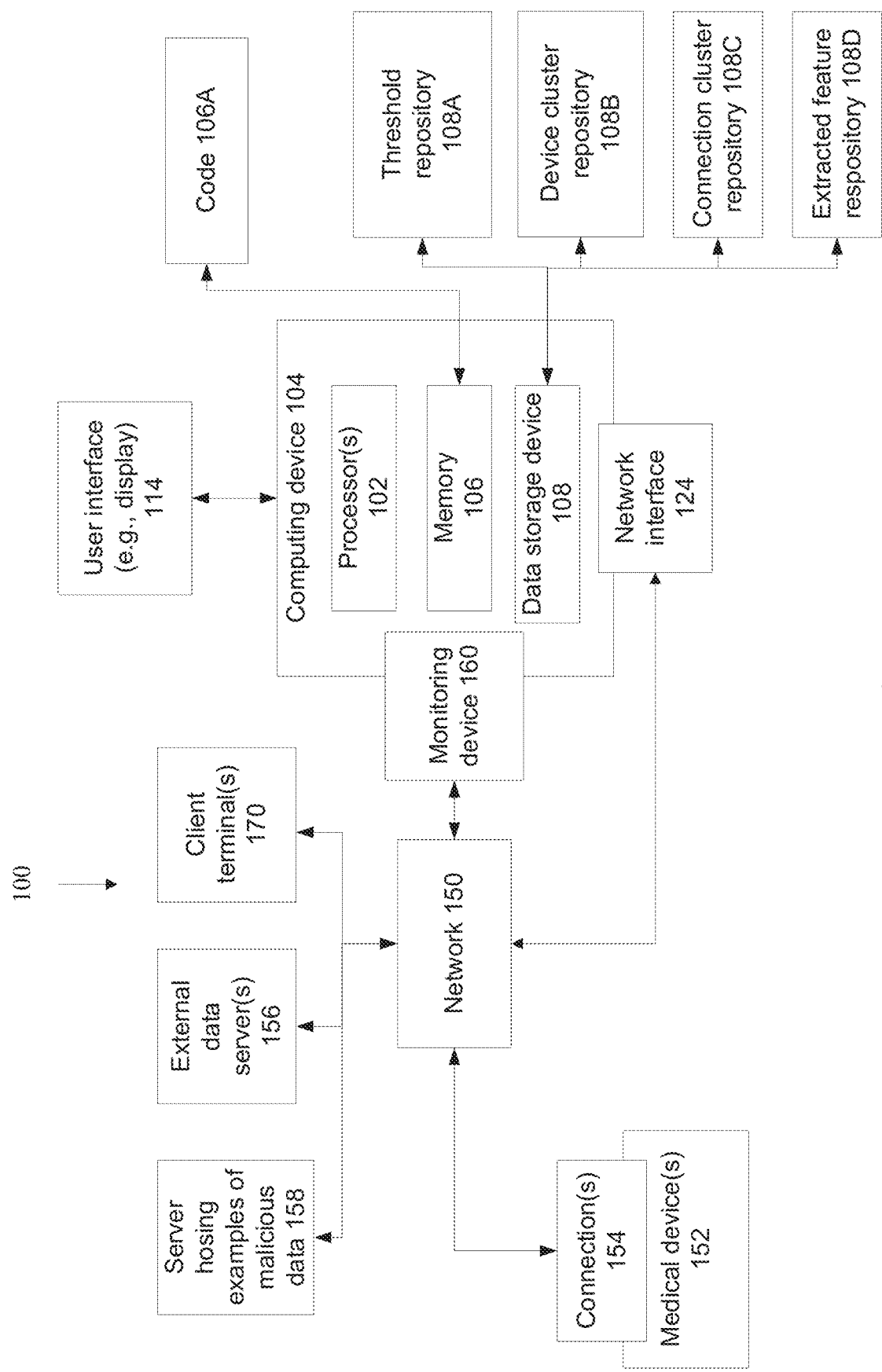
FIG. 1 is a schematic of components of a system for monitoring connection(s) of medical device(s) for detecting likelihood of malicious activity, in accordance with some embodiments of the present invention.

The present invention, in some embodiments thereof, relates to cybersecurity and, more specifically, but not exclusively, to systems and methods for detecting compromised medical devices.

An aspect of some embodiments of the present invention relates to systems, methods, computing devices, and/or code instructions (stored on a data storage device and executable by one or more processors) for detecting a malicious connection of a medical device, for example, a medical device infected by malware, hacked, and the like. A processor, optionally centrally located, monitors packets of network traffic generated by one or more medical devices connected to a network by one or more connections. For each connection of a medical device: the processor selects a device cluster from multiple pre-computed device clusters. The device cluster may be selected according to attributes of the medical device and/or network activity of internal and/or external connection of the medical device. The selected device cluster is associated with multiple connection clusters computed from sample connections of sample medical devices of the selected device cluster, optionally from benign medical devices with benign connections (i.e., not infected with malware and/or not hacked). Multiple categorical features are extracted, optionally from the packets and/or from external data associated with the packets. A distance from the extracted categorical features to a nearest connection cluster of the multiple connection clusters is computed. The distance may represent an amount of similarity between the extracted categorical features and the nearest connection cluster. The connection may be identified as malicious when the distance meets a requirement, for example, the distance is above a threshold, which may mean, for example, that the connection represented by the extracted features is dissimilar from any of the connection clusters representing benign connections.

Optionally, the threshold is set for statistically separating between a distribution of benign distances computed for benign connections of benign medical devices, and malicious distances which may be computed from synthetic data of packets of network traffic that mimic output of malicious connections of malicious medical devices.

At least some implementations of the systems, methods, computing devices, and/or code instructions (stored on a data storage device and executable by one or more processors) described herein address the technical problem of providing cybersecurity for network connected medical devices, by detecting compromised medical devices (e.g., medical devices that are infected with malware and/or medical devices that have been hacked). At least some implementations of the systems, methods, computing devices, and/or code instructions described herein improve the technical field of cybersecurity, by providing approaches for detecting compromised medical devices.

Medical devices are susceptible to vulnerabilities and/or compromise by threat actors like traditional information technology (IT) equipment. Approaches designed for securing traditional IT devices (e.g., laptop, smartphone, server, router, bridge, access point) cannot be applied, and/or are not suitable for securing medical devices. Examples of reasons why standard network security approaches designed traditional IT devices are be simply applied to, and/or unsuitable for medical devices include:

It is technically difficult, or impossible, to install an endpoint protection agent on medical devices.

Upgrading firmware on medical devices is technically challenging.

Access to the underlying operating system of medical devices is usually limited.

Privacy issues, since there is a requirement to protect private information of patients.

Medical devices tend to have communication patterns that are different from traditional IT equipment.

The result is that IT and network security teams have limited visibility and control over the medical devices connected to the network.

At least some implementations of the systems, methods, computing devices, and/or code instructions described herein improve upon prior standard approaches for detecting malicious IT devices. For example:

A knowledge-driven standard approach operates by comparing communication data to known malicious IPs, domains and/or URLs. Such knowledge-driver approaches tend to have low sensitivity. In contrast, at least some embodiments described herein may provide high sensitivity.

A data-driven approach operates by employing classic anomaly detection methods based on historical data of each device. However, such approaches require training by collecting data per device, as well as cleaning the training data since it may contain anomalies in itself. In contrast, at least some embodiments described herein do not necessarily require data of the devices being monitored, enabling monitoring of new devices. It is technically challenging to apply classical methods to many categorical variables compared to numeric variables, which may introduce a high rate of false positives. In contrast, at least some embodiments described herein may use multiple categorical variable without a high false positive rate.

At least some implementations of the systems, methods, computing devices, and/or code instructions described herein provide a solution to the aforementioned technical problem, and/or improve the aforementioned technical field, and/or improve upon the aforementioned prior approaches, by computing a distance for a connection of a medical device, from categorical features to a nearest connection cluster of sample connections of medical devices of a device cluster. The device cluster may be selected according to attributes of the medical device and/or network activity of internal and/or external connection of the medical device. The connection may be identified as malicious when the distance is above a threshold.

Potential advantages by at least some implementations of the systems, methods, computing devices, and/or code instructions described herein include:

Using a centralized network node to detect multiple network connected medical devices (e.g., using packets generated by the medical devices which are sent over the network by communication interfaces of the medical devices).

Protection of privacy of patients. At least some embodiments described herein do not necessarily require accessing the payload of packets, since metadata may be used. Risk of using data that may contain protected healthcare identifiers (PHI) may be reduced or eliminated.

Analysis may be performed in a computing cloud without or with reduced risk of compliance violations.

Suspicious connections of medical devices that may be compromised, may be quickly detected.

High sensitivity of detection.

Use of multiple categorical features. The categorical features may represent a natural way to model outgoing connections from the medical device to the network, for example, in comparison to numerical values which is the standard approach. It is noted that categorical features are technically difficult to use with machine learning and/or data science approaches, and therefore are generally not utilized.

Low false positive rate, even when using multiple categorical features.

Historical data of devices being monitored is not necessarily required.

New medical devices added to the network may be monitored immediately, for example, without collecting historical data first. Anomalies may be detected in new environments initially, without necessarily requiring a dedicated training period.

Dimensionality of data may be reduced, for example, by grouping together common categories. The dimensionality of the data may be reduced while accounting for the innate variability of the data.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Figure 2:
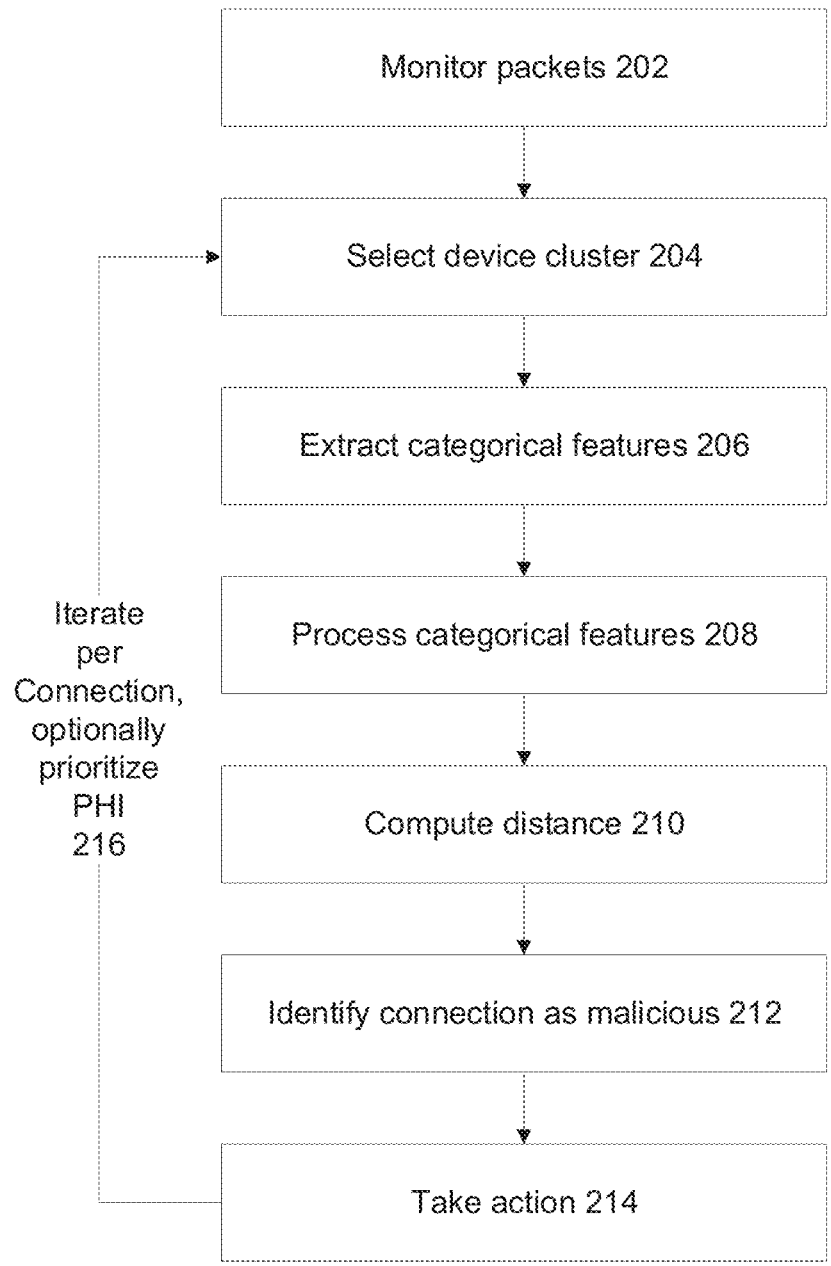
FIG. 2 is a flowchart of a method of detecting a malicious connection of a medical device, in accordance with some embodiments of the present invention.
Figure 3:
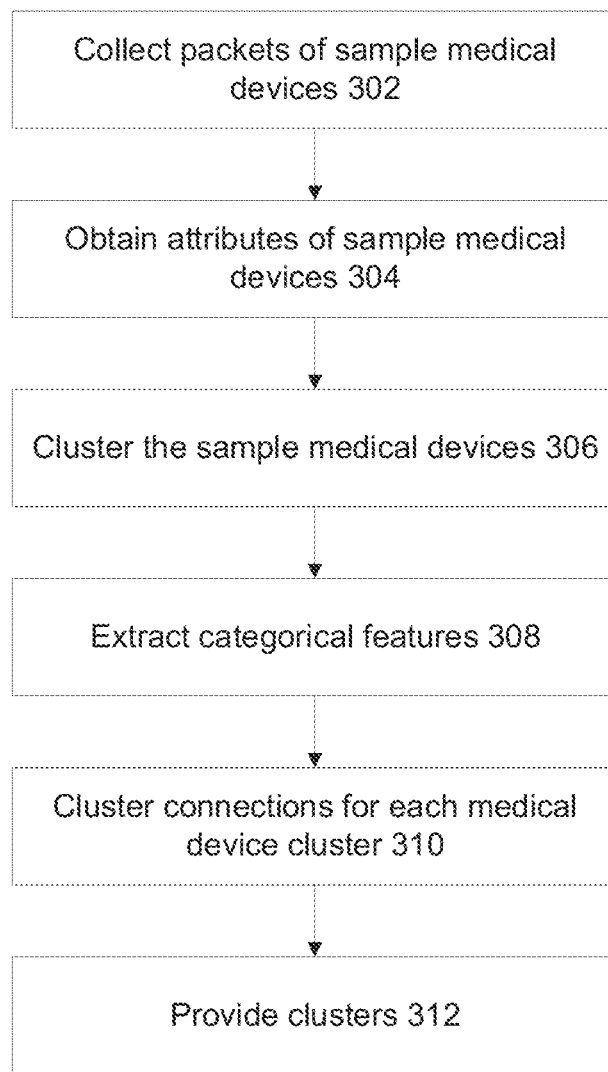
FIG. 3 is a flowchart of a method of computing clusters used for detecting the malicious connection of the medical device, in accordance with some embodiments of the present invention.
Figure 4:
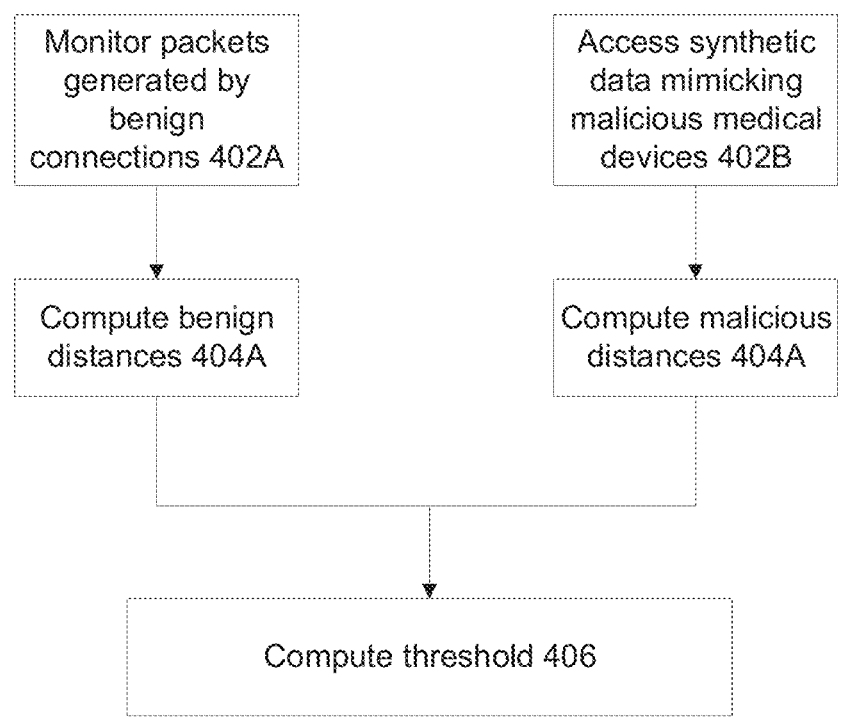
FIG. 4 is a flowchart of a method of computing the threshold of distance used for detecting the malicious connection of the medical device, in accordance with some embodiments of the present invention.
Figure 5:
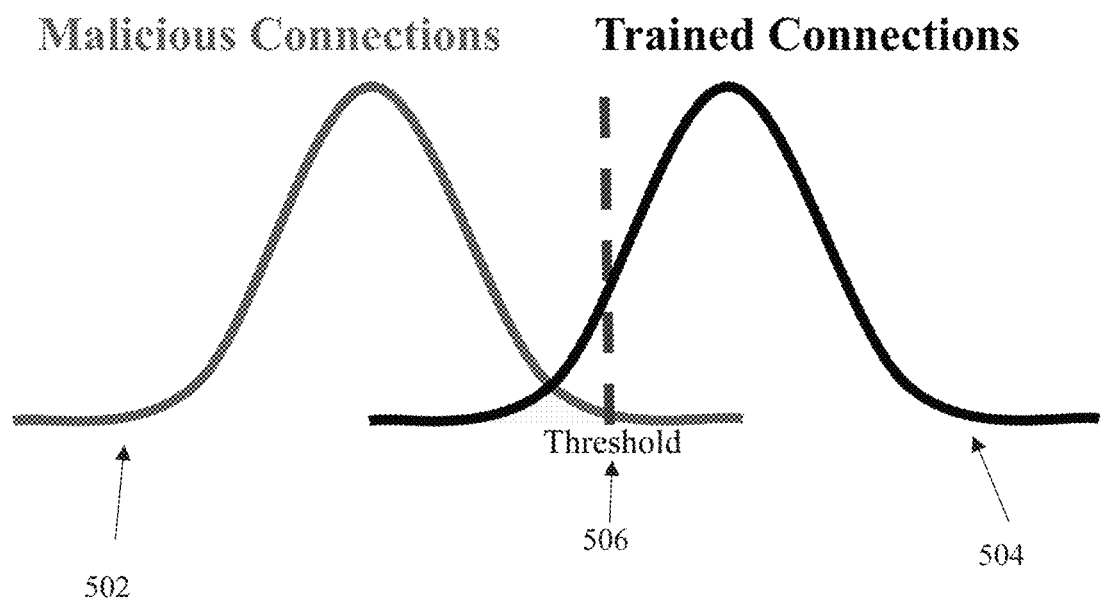
FIG. 5 is a schematic of an exemplary approach for computing a threshold for classifying a distance computed for a connection as benign or malicious, in accordance with some embodiments of the present invention.
Figure 6:
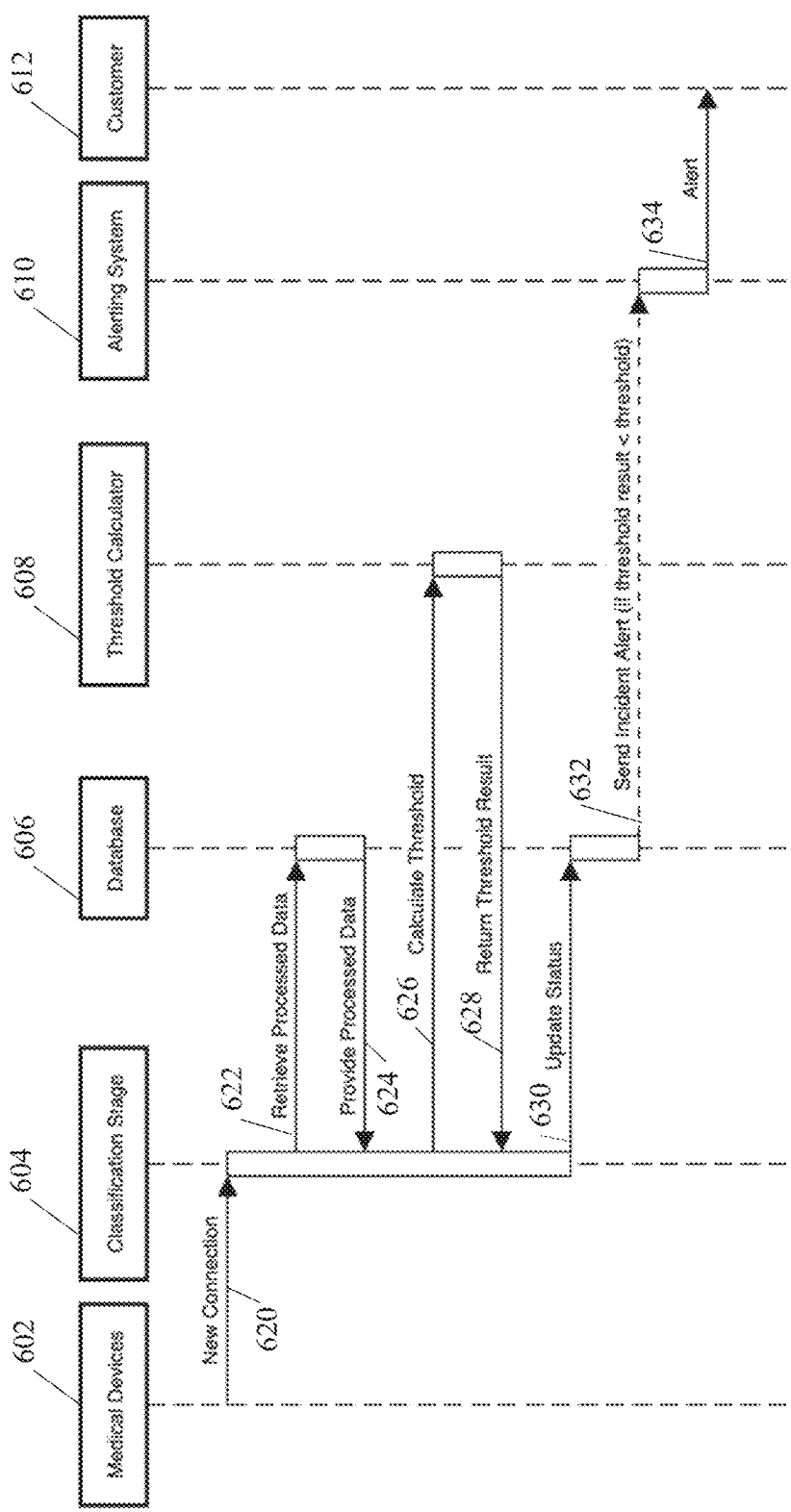
FIG. 6 is a sequence diagram of an exemplary flow for detecting a malicious connection of a medical device, in accordance with some embodiments of the present invention.

Reference is now made to FIG. 1, which is a schematic of components of a system 100 for monitoring connection(s) 154 of medical device(s) 152 for detecting likelihood of malicious activity, in accordance with some embodiments of the present invention. Reference is also made to FIG. 2, which is a flowchart of a method of detecting a malicious connection of a medical device, in accordance with some embodiments of the present invention. Reference is also made to FIG. 3, which is a flowchart of a method of computing clusters used for detecting the malicious connection of the medical device, in accordance with some embodiments of the present invention. Reference is also made to FIG. 4, which is a flowchart of a method of computing the threshold of distance used for detecting the malicious connection of the medical device, in accordance with some embodiments of the present invention. Reference is also made to FIG. 5, which is a schematic of an exemplary approach for computing a threshold for classifying a distance computed for a connection as benign or malicious, in accordance with some embodiments of the present invention. Reference is also made to FIG. 6, which is a sequence diagram of an exemplary flow for detecting a malicious connection of a medical device, in accordance with some embodiments of the present invention.

Reference is also made System 100 may implement the acts of the method described with reference to FIGS. 2-6, by processor(s) 102 of a computing device 104 executing code instructions (e.g., code 106A) stored in a memory (also referred to as a program store).

Computing device 104 monitors packets transmitted over a network 150 by connection(s) 154 of medical device(s) 152, as described herein. A certain medical device(s) 152 may be automatically identified as compromised (e.g., infected with malware, hacked) when a connection 154 of the medical device 152 is identified as likely being malicious, as described herein.

Exemplary medical device(s) 152 include, for example, devices that support a patient (e.g., ventilator, heart-lung machine), devices that analyze the patient (e.g., imaging, ECG), devices that analyze tissue of the patient (e.g., blood gas analyzer), and the like.

Exemplary connection(s) 154 include: connections from a medical device to a Command and Control Server (C2) that is used to control a malware that has been installed on the device, and/or connections from a medical device to an external entity used to store leaking electronic protected health information (ePHI) data that is being exfiltrated from the device.

Computing device 104 is programmed and/or positioned within and/or in communication with network 150 to monitor and/or intercept packets transmitted over network 150 by connection(s) 154 of medical device(s) 152. Computing device 104 may be located in a server farm in communication with network 150. Computing device 104 may be located within a central switch of network 150 through which all packets flow.

Computing device 104 may include and/or be in communication with a network monitoring device 160 for monitoring packet traffic within network 150, for example, a packet sniffer, a packet analyzer, a network sensor, and/or network gateway.

Optionally, computing device 104 monitors and/or intercepts all packets transmitted over network 150. It is noted that computing device 104 may be distributed among multiple devices at different locations in network 150 to monitor and/or intercept all the packets. Alternatively, computing device 104 is installed in a single location, where traffic existing medical device(s) 152 is accessible from the single location.

Computing device 104 may be implemented as, for example one or more and/or combination of: a router, a switch, a network administration server, a group of connected devices, a client terminal, a server, a virtual server, a computing cloud, a virtual machine, a desktop computer, a thin client, a network node, a network server, and/or a mobile device (e.g., a Smartphone, a Tablet computer, a laptop computer, a wearable computer, glasses computer, and a watch computer).

Hardware processor(s) 102 of computing device 104 may be implemented, for example, as a central processing unit(s) (CPU), a graphics processing unit(s) (GPU), field programmable gate array(s) (FPGA), digital signal processor(s) (DSP), and application specific integrated circuit(s) (ASIC). Processor(s) 102 may include a single processor, or multiple processors (homogeneous or heterogeneous) arranged for parallel processing, as clusters and/or as one or more multi core processing devices.

Memory 106 stores code instructions executable by hardware processor(s) 102, for example, a random access memory (RAM), read-only memory (ROM), and/or a storage device, for example, non-volatile memory, magnetic media, semiconductor memory devices, hard drive, removable storage, and optical media (e.g., DVD, CD-ROM). Memory 106 stores code 106A that implements one or more features and/or acts of the method described with reference to FIGS. 2-6 when executed by hardware processor(s) 102.

Computing device 104 may include data storage device(s) 108 for storing data, for example, one or more of: a threshold repository 108A that includes different computed thresholds used for identifying malicious connections, device cluster repository 108B that includes multiple device clusters, connection cluster repository 108C which includes connection clusters for each device cluster, and/or extracted feature repository 108D which includes features extracted from medical devices and/or connections (e.g., for computing the threshold and/or for evaluating a connection for likelihood of being malicious), as described herein. Data storage device(s) 108 may be implemented as, for example, a memory, a local hard-drive, virtual storage, a removable storage unit, an optical disk, a storage device, and/or as a remote server and/or computing cloud (e.g., accessed using a network connection).

Network 150 may be implemented as, for example, a private network, a local area network, a wireless network, a wired network, the internet, a virtual network, a virtual private network, a cellular network, and/or combinations of the aforementioned. For example, network 150 is a network installed in a hospital, ICU, ward, radiology clinic, and/or other healthcare setting, for connecting devices of the healthcare provider.

Computing device 104 includes and/or is in communication with one or more physical user interfaces 114 that include a mechanism for user interaction, for example, to enter data and/or for viewing data such as which medical devices are determined to be likely compromised.

Exemplary physical user interfaces 114 include, for example, one or more of, a touchscreen, a display, gesture activation devices, a keyboard, a mouse, and voice activated software using speakers and microphone.

Computing device 104 may include a network interface 124 for connecting to network 150, for example, one or more of, a network interface card, a wireless interface to connect to a wireless network, a physical interface for connecting to a cable for network connectivity, a virtual interface implemented in software, network communication software providing higher layers of network connectivity, and/or other implementations. It is noted that the network interface 124 of computing device 104 may be integrated with network monitoring device 160.

Computing device 104 may communicate with other devices via network interface 124 connecting to network 150, for example, one or more server(s) hosting examples of malicious data 158 (e.g., used to create synthetic data of emulated infected medical devices for computing thresholds, as described herein), external data server(s) 156 (e.g., used to obtain additional features associated with a connection being monitored), and/or client terminal(s) 170 (e.g., to which an alert indicating a detected compromised medical device is sent).

Referring now back to FIG. 2, at 202, packets of network traffic are monitored. The packets are generated by one or more medical devices connected to a network by one or more connections.

The monitoring may be performed on a centralized node through which the network traffic generated by the medical devices flows. For example, in a server farm architecture, the collection of packets may be done on premise, designed to avoid or reduce ePHI.

Each medical device may be connected to the network via one or more connections.

The connections may be internet facing communications.

The medical devices may be devices for use in diagnosis, treatment, management, and/or prevention of medical conditions and/or diseases. Examples of medical devices include: medical imaging devices (e.g., x-ray, MRI, CT, ultrasound), implantable device (e.g., pacemaker, insulin pump), medical monitor (e.g., ECG machine, blood pressure monitor, blood gas analyzer), support machine (e.g., ventilator, anesthesia device), drug delivery (e.g., IV pump), laboratory equipment (e.g., microscope, spectrometer), and the like.

Optionally, confidentiality compliance is detected. An indication that identifies whether a connection contains protected health information (PHI) or not may be obtained. This may be done in order to ensure compliance with regulations and/or to protect patient confidentiality. This approach may help ensure that privacy regulations are not violated, and/or that safety of patient data is maintained. At least some embodiments described herein are designed to protect patient privacy and/or ensure compliance with relevant regulations.

Features described with reference to 204-216 are performed for each connection identified during the monitoring of the packets.

At 204, a device cluster is selected from multiple device clusters. The device cluster is for the medical device associated with the connection.

An exemplary approach for computing device clusters is described, for example, with reference to FIG. 3.

The device cluster may be selected according to attributes of the medical device and/or network activity of internal and/or external connection of the medical device. Examples of attributes of the medical device include: type of the medical device (e.g., category, such as CT machine, ECG machine, blood gas analyzer, and the like), model of the medical device, manufacturer of the medical device, and operating system running on the medical device.

The attributes of the medical device may be obtained, for example, by analyzing the network traffic of the device and extracting data from protocols that carry the relevant information. In another example, these attributes may be extracted from an external device management system that holds data about each device, such as a computerized maintenance management system (CMMS).

At 206, multiple categorical features are extracted for the connection.

Optionally, the categorical features are extracted without accessing payload of the packets of the network traffic generated by the medical device. The categorical features may be extracted as metadata and/or from metadata. This reduces or eliminates risk of using personal data of patients, which may contain protected healthcare identifiers (PHI), without compliance violations.

Optionally, the categorical features include network features. The network features may be extracted from the raw packets. Exemplary network features include port, transport (TCP or UDP), payload size, source of the connection, destination of the connection, and/or type of data being transmitted.

Alternatively or additionally, the categorical features include enrichment features extracted from external data sources correlated with the packets. For example, geolocation of the external IP address, the protocol of the connection, data about the owner of the IP address space, etc. Examples of external data sources include the WHOIS public dataset that houses information collected when someone registers a domain name or updates their DNS setting, and IP geolocation data.

Alternatively or additionally, the categorical features include expert features calculated based on expert knowledge. For example, an expert knows that a certain connection is related to an anti-virus program being updated from the internet based on the user agent in the connection, which enables adding an "anti-virus update" feature to that connection. For example, tagging a specific IP range as being related to updating an anti-virus agent. This is based on expert knowledge of categorizing connections by user agent.

At 208, the extracted features may be pre-processed.

Optionally, the extracted features are reduced, for example, by performing a dimensionality reduction. The categorical representation of the extracted features may be of a very high dimension, making it computationally inefficient for further processing as described herein. Dimensionality reduction may improve efficiency of computation.

Optionally, a reduced set of features is created by selecting dominant features and excluding non-dominant features from the plurality of categorical features. A dominant feature may appear in at least as many connections as a number of unique labels in the feature to a power of negative one, which may be mathematically represented as:

$$x_{ij} \geq \frac{1}{X_i}$$

$X_i$ is the number of unique level in *feature i*

$x_{ij}$ is the number of times level *j* appears in feature *i*

The distance is computed using the reduced set of features, as described herein.

Alternatively or additionally, categorical features that are missing and/or are non-dominant may be set to a null value. The null value may be represented by a unique value, for example, randomly generated. The random value creates a differentiation between the null values, which may help ensure that two or more null values are similar.

The extracted features, optionally a reduced set of features, may be represented in a format suitable for computation of distance, for example, a vector and/or a point in a multi-dimensional space.

At 210, a distance is computed from the categorical features (optionally the reduced set of features and/or with null value) to a nearest connection cluster of multiple connection clusters. The multiple connection clusters are of sample connections of sample medical devices of the selected device cluster. An exemplary approach for computing the connection clusters is described with reference to FIG. 3.

The distance may be computed from the categorical features to each of the multiple connection clusters. The shortest distance to the nearest connection cluster is identified.

The distance may be computed from a point in a multi-dimensional space, where each dimension represents a certain categorical feature, to a connection cluster of points, where each point represents a different sample connection of a sample medical device. The points in the multi-dimensional space may be represented by the vector representation of the categorical features.

The distance may be computed, for example, using distance metrics from categorical data, such as k-modes.

The distance may be computed from the categorical features to the centroid of each connection cluster.

At 212, connection may be identified (e.g., classified) as malicious (or likely malicious, and/or flagged for further investigation) when the distance meets a requirement, optionally when the shortest distance is above a threshold. The connection may be classified as benign when the shortest distance is below the threshold.

In another example, the connection is fed into a trained machine learning model that outputs a classification category of malicious or benign, for example, as described with reference to FIG. 4.

The distance may represent an amount of similarity between the extracted categorical features and the nearest connection cluster. The connection may be identified as malicious when the connection represented by the extracted features is dissimilar from any of the connection clusters representing benign connections. A large distance, such as above the threshold, may indicate that the connection is not similar to any of the connection clusters, suggesting that the connection is malicious.

An exemplary approach for computing the threshold is described, for example, with reference to FIG. 4.

At 214, one or more actions may be triggered in response to identifying the connection as malicious. Exemplary actions include:

Generating instructions for isolating the medical device from other devices on the network.

Triggering an anti-malware process for automatically detecting and removing malware from the medical device.

Shutting down the medical device.

Switching a patient from the malicious medical device for another medical device.

Generating an alert, for example, a message to a mobile device of a technician, a pop-up on a screen of an administrative server, and logging the alert in a log. The generation of alerts upon the detection of suspicious connections may help quickly identify and respond to potential security threats. The alert may help a user to distinguish whether the connection constitutes a security threat or can be disregarded safely.

At 216, one or more features described with reference to 202-212 are iterated. The iterations may be performed per connection. The iterations may be performed over time, to provide monitoring of the network, optionally continuously. The continuous monitoring for suspicious connections enables healthcare organizations to secure their networks, safeguarding their data and systems in the process.

Optionally, an indication of whether protected health information (PHI) is sent and/or received over the connection of the medical device, is determined. Optionally, the indication of PHI is determined for each connection. Connections of medical devices that send and/or receive PHI may be prioritized over other connections over which PHI is not sent and/or received. Prioritizing processing of connections over which PHI is sent and/or received may stop and/or prevent compliance violations, which may be in addition to security issues.

Referring now back to FIG. 3, at 302, packets sent by sample connections of sample medical devices over a network are collected. The collection may be done at a central location (e.g., cloud, central node), and/or distributed at multiple different locations (e.g., different nodes such as for different private networks and/or at different facilities).

Optionally, packets are collected from different medical devices which may be from different healthcare organizations and/or within different environments. For example, medical devices of different hospitals, different clinics, installed in different geographical locations, and the like. The medical devices may have different attributes, for example, different types of medical devices (e.g., CT, blood gas analyzer, ventilator, heart lung machine, ultrasound), different models, different manufacturers, and/or running different operating systems.

Using data across different devices and/or environments, may help to generalize to a wide range of situations. The collective data may form the foundation for the creation of benign connection clusters. This approach allows for a more robust method that may be able to accurately identify and classify connections in diverse healthcare environments.

The sample medical devices and the sample connections may be benign. The sample medical devices and/or the sample connections may exclude malicious connections and/or may exclude compromised medical devices. The sample medical devices and/or the sample connection may be known to be non-infected with malware and/or non-hacked.

At 304, attributes of the sample medical devices are obtained. Network activity of internal and/or external connections of the sample medical device may be obtained. Additional details of attributes are described, for example, with reference to 204 of FIG. 2.

At 306, the sample medical devices are clustered into multiple device clusters according to the attributes of the sample medical devices, and/or network activity of internal and/or external connections of the sample medical device.

Clustering medical devices by their attributes and/or network activity is done so that medical devices that are similar and/or operate in a similar way are clustered together.

Each device cluster may include one or more sample medical devices that are similar to one another, for example, different CT machines of different manufacturers, imaging machines that include CT, MRI, and ultrasound, and/or medical devices of different types manufactured by the same manufacturer and therefore having attributes.

At 308, categorical features are extracted for each connection, for example, as described with reference to 206 of FIG. 2. The categorical features may be extracted, for example, in parallel to the clustering of the sample medical devices, prior to the clustering, and/or after the clustering.

The categorical features may be processed, for example, as described with reference to 208 of FIG. 2.

At 310, multiple connection clusters are computed for each respective device cluster.

The connection clusters may be computed by clustering categorical features extracted for each sample connection of each sample device of the respective device cluster. A clustering process designed for clustering categorical features may be used, for example, an extension of the k-modes process.

Each connection cluster may include sample connections of the device cluster that are similar to each other in terms of similar categorical features.

Each connection cluster may include a centroid, which may be used for computing distance, as described herein.

At 312, the device clusters and corresponding connection clusters are provided for computing distance for detecting malicious connections, as described herein. Each device cluster includes multiple connection clusters each representing connections of a certain type.

Referring now back to FIG. 4, at 402A, packets of network traffic generated by benign medical devices connected to the network by benign connections (i.e., not infected by malware, and/or not hacked) are monitored, for example, as described with reference to 202 of FIGS. 2 and/or 302 of FIG. 3.

At 404A, multiple benign distances are computed for the benign connections. Each benign distance may be computed by implementing features described with reference to 204-210 of FIG. 2 for each benign connection.

At 402B, packets of network traffic generated by malicious medical devices connected by malicious connections are obtained. The packets may be obtained by accessing synthetic data of packets of network traffic that mimics output of malicious medical devices infected by malware and/or hacked. Synthetic data may be obtained, for example, from open-source threat-intelligence platforms.

At 404B, multiple malicious distances are computed for the malicious connections. Each malicious distance may be computed by implementing features described with reference to 204-210 of FIG. 2 for each malicious connection.

At 406, a requirement for classifying a certain distance as benign or malicious is determined.

The requirement may be a threshold, such as where a certain distance is classified as benign when below the threshold, and malicious when above the threshold.

The threshold may be selected for statistically separating between a distribution of the benign distances and the malicious distances.

The threshold may be selected by computing a similarity score indicating similarity between each of the malicious distances and the benign distances. A certain malicious distance having a maximum similarity with a certain benign distance is identified. The threshold is set as the certain malicious distance.

The threshold may be computed by computing the distribution of minimum distances of the (e.g., synthetic) malicious connections, and the distribution of the distances of the benign connections. The maximum similarity score for the synthetic connection sets the minimum threshold, where distances of connections below the threshold are classified as malicious.

The requirement may be a machine learning model that is trained on a training dataset of distances, each labeled with a ground truth label of benign or malicious. The machine learning model classifies an input distance into benign or malicious. Exemplary architectures of machine learning models include: a classifier, a support vector machine, a neural network, and a random forest based approach.

Referring now back to FIG. 5, an exemplary distribution of distances computed for malicious connections 502, optionally based on synthetic data, is presented. Another exemplary distribution of distances computed for benign connections 504, in presented. A threshold 506 that statistically separates between distribution 502 and distribution 504 may be selected and/or computed.

Referring now back to FIG. 6, the sequence diagram may include one or more components described with reference to system 100 of FIG. 1, and/or be based on one or more features described with reference to FIGS. 2-5, and/or other features described herein.

The exemplary flow depicted with reference to FIG. 6 is optionally between a medical device 602 (e.g., as described with reference to medical device 152 of FIG. 1), a classification stage 604, a database 606, a threshold calculator 608, an alerting system 610, and/or a customer 612. Classification stage 604, threshold calculator 608 and/or alerting system 610 may be implemented by, for example, one or more of: code 106A, memory 106, data storage device 108 that includes one or more of 108A, 108B, 108C, and/or 108D, and/or processor(s) 102 of computing device 104, as described with reference to FIG. 1. Database 606 may be implemented by, for example, one or more of: code 106A, memory 106, data storage device 108 that includes one or more of 108A, 108B, 108C, and/or 108D, server(s) 158 and/or 156, and/or processor(s) 102 of computing device 104, as described with reference to FIG. 1. Threshold calculator 608 may be implemented by, for example, one or more of: code 106A, memory 106, data storage device 108 that includes one or more of 108A, 108B, 108C, and/or 108D, and/or processor(s) 102 of computing device 104, as described with reference to FIG. 1. Alerting system 610 may be implemented by, for example, one or more of: code 106A, memory 106, processor(s) 102 of computing device 104, and/or client terminal 170, as described with reference to FIG. 1. Customer 612 may be implemented by, for example, one or more of: code 106A, memory 106, processor(s) 102 of computing device 104, and/or client terminal 170, as described with reference to FIG. 1.

At 620, a new connection by a medical device is processed. The new connection may be an entirely new connection of a new medical device connected to the network. Alternatively or additionally, the new connection is of an existing medical device that established a new connection to the network. Alternatively or additionally, the new connection is an existing connection of an existing medical device that is being monitored.

At 622, a request to retrieve processed data of the new connection is generated. The retrieved processed data may be, for example, attributes of the medical device and/or network activity of internal and/or external connections of the medical device, and/or categorical features, for example, as described herein.

At 624, the processed data is obtained.

At 626, a request to calculate a threshold result for the new connection is generated. The threshold is calculated by selecting a device cluster according to attributes of the medical device and/or network activity of internal and/or external connection of the medical device, and computing a distance from the categorical features to a nearest connection cluster of connection clusters of sample connections of medical devices of the selected device cluster, and identifying the connection as malicious when the distance is above a threshold, for example, as described herein.

At 628, the threshold result, indicating whether the connection is malicious or not according to whether the distance for the new connection is above or below the threshold, is returned.

At 630, a status of the new connection may be updated, for example, in a database. The status may indicate whether the new connection is found to be suspicious for being malicious or not.

At 632, an incident alert may be generated when the connection is found to be likely malicious, such as when the distance for the new connection is greater than the threshold, for example, as described herein. The incident alert may be sent to the alerting system.

At 634, an alert may be sent to the customer, for example, indicating that the medical device with the new connection is found to be likely malicious, which may warrant further investigation and/or trigger an automated process for removing malware and/or isolating the medical device, for example, as described herein.

Various embodiments and aspects of embodiments described herein as delineated hereinabove and as claimed in the claims section below find support in the following exemplary use-case.

EXAMPLES

Reference is now made to the following exemplary use-case, which together with the above descriptions illustrate some embodiments in a not necessarily limiting fashion.

Use Case: Detection of Compromised Blood Gas Analyzer in a Critical Care Unit (ICU)
Introduction In a critical care unit, the proper functioning of medical devices is essential for the well-being of patients. Blood gas analyzers are critical devices used to measure the pH, electrolyte levels, and gas content of blood samples. In this use case, the efficacy of a system based on embodiments described herein is demonstrated for detecting a compromised blood gas analyzer that runs on the Windows operating system.

Detection of Suspicious Connection:

The Blood Gas Analyzer system connections are monitored as described herein, and the relevant device model is employed to evaluate new connections. The system based on embodiments described herein compares each new connection to the selected centroids of the cluster, and associated threshold of the Blood Gas Analyzer device model. When a new connection fails to meet the threshold criteria, the corresponding medical device is flagged as suspicious and undergoes further evaluation.

Threshold Evaluation:

In this example, the suspicious connection had an unknown location, Sri Lanka, and was using an unusual port (SSH Port 22) that is not commonly used by Blood Gas Analyzer devices for external internet communication. These factors caused the system to be unable to find a matching cluster for the connection in question. The similarity score (i.e., distance) between the connection and the Blood Gas Analyzer clusters was below the established threshold, indicating the potential presence of malicious activity.

Generation of Alert:

Based on the above findings, an alert was generated and sent for further investigation. Upon review of the device network, a malware infection was discovered and isolated, allowing for the removal of the threat and the safeguarding of sensitive patient information.

Conclusion:

The use of the system based on embodiments described herein is effective for detecting and/or mitigating potential threats to medical devices. In this scenario, the system was able to identify a suspicious connection made to the Blood Gas Analyzer and trigger a response that led to the prevention of a larger attack and to the quarantine of this specific device.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

It is expected that during the life of a patent maturing from this application many relevant medical devices will be developed and the scope of the term medical device is intended to include all such new technologies a priori.

As used herein the term "about" refers to ±10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

It is the intent of the applicant(s) that all publications, patents and patent applications referred to in this specification are to be incorporated in their entirety by reference into the specification, as if each individual publication, patent or patent application was specifically and individually noted when referenced that it is to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A computer implemented method of detecting a malicious connection of a medical device, comprising:
   monitoring packets of network traffic generated by a plurality of medical devices connected to a network by a plurality of connections;
   for a connection of a medical device:
      selecting a device cluster from a plurality of device clusters according to attributes of the medical device and/or network activity of internal and/or external connection of the medical device;
      extracting a plurality of categorical features;
      computing a distance from the plurality of categorical features to a nearest connection cluster of a plurality of connection clusters of sample connections of sample medical devices of the selected device cluster; and
      identifying the connection as malicious when the distance is above a threshold.

2. The computer implemented method of claim 1, further comprising, determining whether protected health information (PHI) is sent and/or received over the connection of the medical device, and prioritizing the connection of the medical device over other connections over which PHI is not sent and/or received.

3. The computer implemented method of claim 1, further comprising in response to identifying the connection as malicious, generating instructions for isolating the medical device from other devices on the network.

4. The computer implemented method of claim 1, further comprising:
   computing the plurality of device clusters by clustering a plurality of sample medical devices according to attributes of each sample medical device, and/or network activity of internal and/or external connections of each sample medical device;
   for each respective device cluster, computing the plurality of connection clusters by clustering categorical features extracted for each sample connection of each sample device of the respective device cluster.

5. The computer implemented method of claim 1, wherein the medical device are selected from a group including: type of the medical device, model of the medical device, manufacturer of the medical device, and operating system running on the medical device.

6. The computer implemented method of claim 1, wherein the sample medical devices and the plurality of sample connections are benign and exclude malicious connections and compromised medical devices.

7. The computer implemented method of claim 6, wherein the plurality of sample medical devices are at least one of: from different healthcare organization, and from different environments.

8. The computer implemented method of claim 1, further comprising computing the threshold by:
   monitoring packets of network traffic generated by a plurality of benign medical devices connected to the network by a plurality of benign connections not infected by malware;
   computing a plurality of benign distances for the plurality of benign connections, each benign distance computed by the selecting the device, the extracting, and the computing the distance;
   accessing synthetic data of packets of network traffic that mimics output of malicious medical devices infected by malware to a plurality of malicious connections;
   computing a plurality of malicious distances for the plurality of malicious connections, each malicious distance computed by the selecting the device, the extracting, and the computing the distance; and
   setting the threshold for statistically separating between a distribution of the plurality of benign distances and the plurality of malicious distances.

9. The computer implemented method of claim 8, wherein setting the threshold comprises computing a similarity score indicating similarity between each of the plurality of malicious distances and the plurality of benign distances,
   identifying a certain malicious distance having a maximum similarity with a certain benign distance, and
   setting the threshold as the certain malicious distance.

10. The computer implemented method of claim 1, wherein the plurality of features are extracted without accessing payload of the packets of the network traffic generated by the plurality of medical devices.

11. The computer implemented method of claim 1, wherein the monitoring is performed on a centralized node through which the network traffic generated by the plurality of medical devices flows.

12. The computer implemented method of claim 1, wherein the plurality of categorical features include network features extracted as metadata from the packets.

13. The computer implemented method of claim 1, wherein the plurality of categorical features include enrichment features extracted from external data sources correlated with the packets.

14. The computer implemented method of claim 1, wherein the plurality of categorical features include expert features calculated based on expert data.

15. The computer implemented method of claim 1, wherein the plurality of medical devices are selected from a group including: imaging devices, ventilators, blood gas analyzers, ECG monitors.

16. The computer implemented method of claim 1, further comprising:
   creating a reduced set of features by selecting dominant features and excluding non-dominant features from the plurality of categorical features,
   wherein a dominant feature appears in at least as many connections as a number of unique labels in the feature to a power of negative one,
   wherein the distance is computed using the reduced set of features.

17. The computer implemented method of claim 1, further comprising setting values of the plurality of categorical features that are missing and/or are non-dominant to a unique value that is randomly generated.

18. A system for detecting a malicious connection of a medical device, comprising:
   at least one processor executing a code for:
      monitoring packets of network traffic generated by a plurality of medical devices connected to a network by a plurality of connections;

for a connection of a medical device:
- selecting a device cluster from a plurality of device clusters according to attributes of the medical device and/or network activity of internal and/or external connection of the medical device;
- extracting a plurality of categorical features;
- computing a distance from the plurality of categorical features to a nearest connection cluster of a plurality of connection clusters of sample connections of sample medical devices of the selected device cluster; and
- identifying the connection as malicious when the distance is above a threshold.

19. A non-transitory medium storing program instructions for detecting a malicious connection of a medical device, which when executed by at least one processor, cause the at least one processor to:

monitor packets of network traffic generated by a plurality of medical devices connected to a network by a plurality of connections;

for a connection of a medical device:
- select a device cluster from a plurality of device clusters according to attributes of the medical device and/or network activity of internal and/or external connection of the medical device;
- extract a plurality of categorical features;
- compute a distance from the plurality of categorical features to a nearest connection cluster of a plurality of connection clusters of sample connections of sample medical devices of the selected device cluster; and
- identify the connection as malicious when the distance is above a threshold.

* * * * *